United States Patent [19]
Kitagawara et al.

[11] Patent Number: 5,302,832
[45] Date of Patent: Apr. 12, 1994

[54] METHOD FOR EVALUATION OF SPATIAL DISTRIBUTION OF DEEP LEVEL CONCENTRATION IN SEMICONDUCTOR CRYSTAL

[75] Inventors: Yutaka Kitagawara; Ryoji Hoshi; Takao Takenaka, all of Gunma, Japan

[73] Assignee: Shin-Etsu Handotai Co., Ltd., Tokyo, Japan

[21] Appl. No.: 950,677

[22] Filed: Sep. 25, 1992

[30] Foreign Application Priority Data

Sep. 26, 1991 [JP] Japan ................................. 3-274545

[51] Int. Cl.$^5$ .......................................... G01N 21/63
[52] U.S. Cl. ................................................ 250/459.1
[58] Field of Search ..................... 257/48; 250/459.1

[56] References Cited

U.S. PATENT DOCUMENTS

| | | | |
|---|---|---|---|
| Re. 32,821 | 1/1989 | Auth ................................ | 250/458.1 |
| 3,748,579 | 7/1973 | Henry et al. .................... | 324/158 D |
| 4,492,871 | 1/1985 | Tajima ............................ | 250/459.1 |

FOREIGN PATENT DOCUMENTS 2-192751  7/1990  Japan ................................ 250/459.1

*Primary Examiner*—Constantine Hannaher
*Attorney, Agent, or Firm*—Ronald R. Snider

[57] ABSTRACT

Spatial distribution of deep level concentration near the surface of a semiconductor wafer is evaluated quickly and accurately by a method which comprises at least a step of scanning the surface of the semiconductor wafer in the X and Y direction with a laser beam for carrier excitation from a laster beam source in accordance with the room-temperature photoluminescence (PL) process thereby measuring the wafer map ($M_D$) of deep level PL intensity ($I_D$) and wafer map ($M_B$) of band edge PL intensity ($I_B$) in the semiconductor wafer and a step of dividing the wafer map ($M_D$) of PL intensity ($I_D$) by the $\nu$'th power of the wafer map ($M_B$) of PL intensity ($I_B$) {the magnitude of the $\nu$'th power presenting the numerical value obtained by empirically confirming the dependence of the band edge PL intensity ($I_B$) on the power of the excitation laster mean} thereby determining the spatial distribution ($M_N$) of the relative value of deep level concentration ($N_D$) and performing the evaluation of the distribution of relative deep level concentration on the basis of the spatial distribution ($M_N$) of the relative deep level concentration ($N_D$).

1 Claim, 10 Drawing Sheets $M_B$ $M_D$ $\dfrac{M_D}{M_B^{1/2}}$

METHOD FOR EVALUATION OF SPATIAL DISTRIBUTION OF DEEP LEVEL CONCENTRATION IN SEMICONDUCTOR CRYSTAL

BACKGROUND OF THE INVENTION

1. FIELD OF THE INVENTION

This invention relates to a method for the evaluation of spatial distribution of deep level concentration in a semiconductor crystal and more particularly to improvements in and concerning a method for the evaluation of the spatial distribution of relative deep level concentration near the surface of a semiconductor wafer.

2. DESCRIPTION OF THE PRIOR ART

Heretofore, the method of photoluminescence has been employed for the study on deep level in the semiconductor crystal of a semiconductor wafer. The measurement of photoluminescence (PL) of semiconductor crystals is predominantly carried out at low temperatures such as the temperature of liquid nitrogen or that of liquid helium. In silicon crystals, only the low-temperature measurement has been performed effectively. In the low-temperature measurement, however, numerous deep luminescence levels and dopant levels originate in complicated mechanism of luminescence and defy analysis.

Recently, Tajima et al. developed a technique for enhancing the sensitivity of measurement of photoluminescence (hereafter abbreviated to PL) [M. Tajima, Jpn. J. Appl. Phys. 27, L1323–L1326 (1988)]. Owing to this technique, the observation of deep level PL spectrum at room temperature and the wafer mapping of PL intensity in a wafer which have been difficult to attain to date can be carried out with high sensitivity and with ease. The PL spectrum obtained by the room temperature PL measurement generally consists of one deep level luminescence having a PL intensity of $I_D$ at a wavelength of $\lambda_D$ and one band edge luminescence having a PL intensity of $I_B$ at a wavelength of $\lambda_B$ as illustrated in FIG. 2. In this case the mechanism of luminescence is conspicuously simple as compared with that which is involved in the low-temperature measurement. With respect to the deep level called EL2 in a semiinsulating ($10^7$–$10^9$ $\Omega$cm) GaAs crystal, therefore, it has been demonstrated that a strong correlation exists between the intensity $I_D$ of the deep level PL and the deep level concentration $N_D$ [M. Tajima, Appl. Phys. Lett. 53, 959–961(1988)]. In short, the relation of $I_D \alpha N_D$ is approximately satisfied in this case.

Incidentally, however, the intensity $I_D$ of deep level PL at room temperature is not always proportional to the deep level concentration $N_D$. Generally, it has been known that this intensity $I_D$ is approximately proportional to the product of the deep level concentration $N_D$ multiplied by the carrier lifetime $\tau$ and is expressed as $I_D \alpha N_D \tau$. The result of the deep level (EL2) in GaAs reported by Tajima is considered to represent a special case in which $\tau \approx$ constant in the expression of $I_D \alpha N_D \tau$ is acceptable. Generally with respect to deep levels in semiconductors, however, there exist numerous cases in which the expression $\tau \approx$ constant is not satisfied. With respect to the deep level PL (P-line) related to the thermal donor in the Si crystal and the deep level PL (D1-line) related to the precipitation of oxygen in the Si crystal, for example, it occurs not infrequently that the expression $\tau \approx$ constant cannot be admitted as true and the proportional relation between $I_D$ and $N_D$ is not recognized.

When the spatial $I_D$ data of a semiconductor wafer are obtained by measurement and are subjected to mapping, the outcome of the mapping does not always correspond to the distribution of the deep level concentration $N_D$.

SUMMARY OF THE INVENTION

This invention, conceived in the urge to solve the drawbacks of the prior art described above, has as an object thereof the provision of a method which is capable of obtaining spatial distribution of relative deep level concentration near the surface of a semiconductor wafer.

To accomplish the object described above according to this invention, there is provided a method for the evaluation of spatial distribution of deep level concentration in the semiconductor crystal, which method comprises obtaining a wafer map ($M_D$) of deep level PL intensity ($I_D$) in the semiconductor wafer and a wafer map ($M_B$) of band edge PL intensity ($I_B$) in the wafer, then dividing the former map ($M_D$) of the PL intensity ($I_D$) in the wafer by the $\nu$'th power of the latter map ($M_B$) of the PL intensity ($I_B$) in the wafer thereby finding the spatial distribution of relative deep level concentration ($N_D$) in the wafer, and evaluating the distribution of the relative deep level concentration in accordance with the spatial distribution ($M_N$) of relative deep level concentration in the wafer.

To be specific, this invention is directed to a method for the evaluation of spatial distribution of deep level concentration near the surface of the semiconductor wafer under test, characterized by comprising at least a step of scanning the surface of the semiconductor wafer in the X and Y directions with a laser beam for carrier exitation from a laser beam source in accordance with the room-temperature photoluminescence (PL) process thereby measuring wafer map ($M_D$) of deep level PL intensity ($I_D$) and wafer map ($M_B$) of band edge PL intensity ($I_B$) in the semiconductor wafer and a step of dividing the map ($M_D$) by the $\nu$'th power of the map ($M_B$) of PL intensity ($I_B$) {the magnitude of the $\nu$'th power representing the numerical value obtained by empirically confirming the dependence of the PL intensity ($_B$) on the power of the exitation laser beam} thereby determining the spatial distribution ($M_N$) of the relative value of deep level concentration ($N_D$) and performing the evaluation of the distribution of relative deep level concentration on the basis of the spatial distribution ($M_N$) of the relative deep level concentration.

BRIEF DESCRIPTION OF THE DRAWINGS

This invention will be better understood and objects other than those set forth above will become apparent when consideration is given to the following detailed description thereof. This description makes reference to the annexed drawings wherein:

FIG. 4b is a plane view illustrating in monochromic concentration the intensity distribution of $I_B$ in the map ($M_B$) of FIG. 4a.

DETAILED DESCRIPTION OF THE PREFERRED EMBODIMENTS

Figure 1:
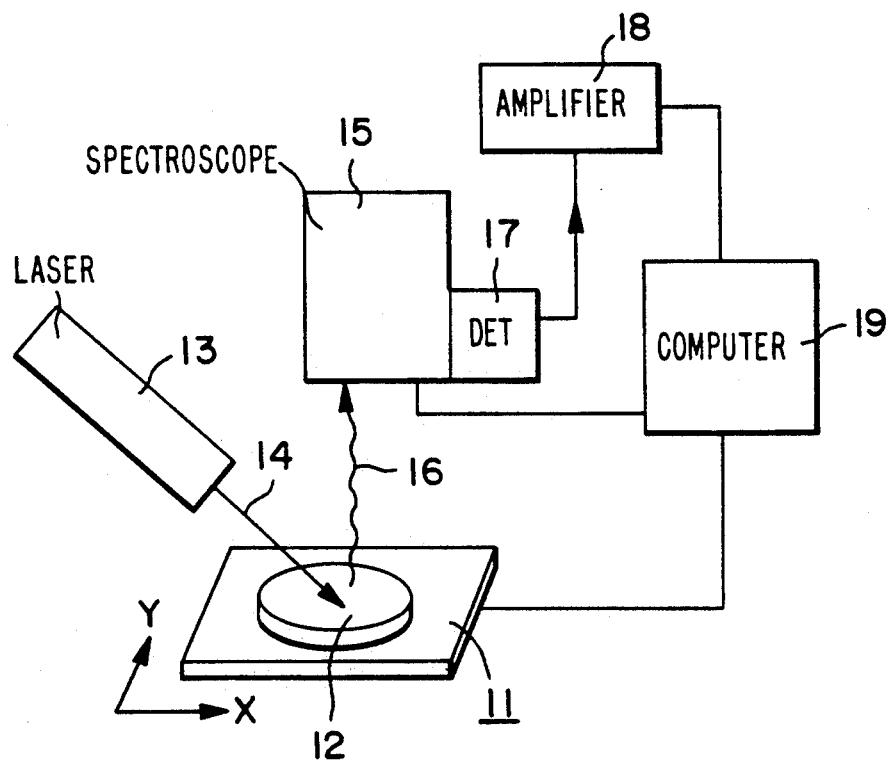
FIG. 1 is a schematic block diagram illustrating a constructional example of an apparatus of evaluation for specifically working the method of evaluation of this invention.

When the wafer map ($M_D$) of the deep level PL intensity ($I_D$) and the wafer map ($M_B$) of the band edge intensity ($I_B$) in a semiconductor wafer are measured and the map ($M_D$) is divided by the $\nu$'th power of the map ($M_B$), the quotient is in proportion to the wafer map $M_N$ of the relative deep level concentration $N_D$. By the following [formula 1], therefore, $M_N$ determines the spatial distribution of relative concentration of deep level defect (D1-line defect) in the wafer induced by oxygen precipitation in the CZ-grown Si single crystal, for example. Generally, since the D1-line defect concentration is closely related with the amount of precipitated oxygen ($\Delta[Oi]$) and has an approximately proportional relation therewith, $M_N$ satisfactorily reflects a spatial distribution of the amount of precipitated oxygen in the wafer.

$$M_n \propto \frac{M_D}{M_B^\nu} \quad \text{[Formula 1]}$$

Now, the method contemplated by this invention for the evaluation of spatial distribution of deep level concentration near the surface of the semiconductor wafer will be described in detail below.

As described previously, the deep level PL intensity ($I_D$) and the band edge PL intensity ($I_B$) manifested with photoluminescence (PL) in a semiconductor wafer are obtained by observing the spectrum of photoluminescence (PL) at room temperature. The room-temperature PL process enables the mappings ($M_D$) and ($M_B$) of the relevant PL intensities ($I_D$) and ($I_B$) by scanning the semiconductor wafer surface under test manipulated on the X-Y stage with an excitation laser beam from a laser beam source.

In this case, the deep level PL mentioned above results from the carrier recombination through a deep level at room temperature. The intensity ($I_D$) of the deep level PL is not always proportional to the deep level concentration ($N_D$). Generally, it is held that this intensity ($I_D$) is proportional to the product of the concentration ($N_D$) multiplied by the carrier lifetime ($\tau$) as indicated by the following expression:

$$[I_D \alpha N_D \tau] \quad (1)$$

In the meantime, the band edge PL mentioned above results from the carrier recombination taking place between the conduction band and the valence band. It is held that the intensity ($I_B$) thereof is proportional to the n'th power (n generally standing for a value in the range between 1 and 2) of the carrier life time ($\tau$) as indicated by the following expression:

$$[I_B \alpha \tau^n] \quad (2)$$

In this case, what is actually necessary for the evaluation of the distribution of deep level concentration in the semiconductor wafer is the spatial distribution ($M_N$) of $N_D$.

In the method of the present embodiment, therefore, the following expression will be derived from the expression of proportionality (1) mentioned above:

$$N_D \alpha I_D/\tau$$

and the following [formula 2] from the expression of proportionality (2):

$$N_D \alpha I_B^{1/n} = I_B^\nu (\nu = 1/n) \quad \text{[Formula 2]}$$

Here, $N_D$ is expressed as indicated by the [formula 3] and the map ($M_N$) in the wafer of the deep level concentration $N_D$ as indicated by the [formula 4].

$$N_D \alpha I_D/I_B^\nu \quad \text{[Formula 3]}$$

$$M_N \alpha M_D/M_B{}^\nu \quad \text{[Formula 4]}$$

Incidentally, the numerical value of $\nu$ (generally falling in the range between 0.5 and 1) can be found by empirically confirming the dependence of the band edge PL intensity ($I_B$) on the power of the excitation laser beam.

Specifically in the method of the present embodiment, the spatial distribution in the wafer ($M_N$) of the relative value of the deep level concentration is found by dividing the map in the wafer ($M_D$) of the deep level PL intensity ($I_D$) by the $\nu$'th power of the map in the wafer ($M_B$) of the band edge PL intensity ($I_B$) {the numerical value of the $\nu$'th power being obtained by empirically determining the dependence of the band edge PL intensity ($I_B$) on the power of the excitation laser beam and generally falling in the range between 0.5 and 1.01 as indicated by formula 5 and the distribution of relative deep level concentration is evaluated on the basis of the spatial distribution in the wafer ($M_N$) of the relevant relative value of the deep level concentration. As a result, the spatial distribution of the relative value of deep level concentration in a given semiconductor wafer can be simply and easily evaluated by the operation which has no use for either contact with or breakage of the sample.

$$(M_D/M_B \nu) \quad \text{[Formula 5]}$$

FIG. 1 is a schematic block diagram illustrating a constructional example of an apparatus of evaluation to be used for specifically working the method of evaluation contemplated by this invention.

In the apparatus constructed as illustrated in FIG. 1, 11 stands for an X-Y stage which can be driven as controlled in the two directions of X and Y, 12 for a semiconductor wafer mounted and retained as a sample on the X-Y stage 11, 13 for a laser beam source to irradiate an excited laser beam 14 on the semiconductor wafer 12, 15 for a spectroscope serving the purpose of dispersing a photoluminescence light 16 emanating from the semiconductor wafer 12, 17 for a detector for PL light from the spectroscope 15, 18 for an amplifier adapted to amplify the electrical signal of the PL from the detector 17, and 19 for a computer to be used for controlling the mechanical operation of the apparatus and carrying out arithmetic processing.

Figure 2:
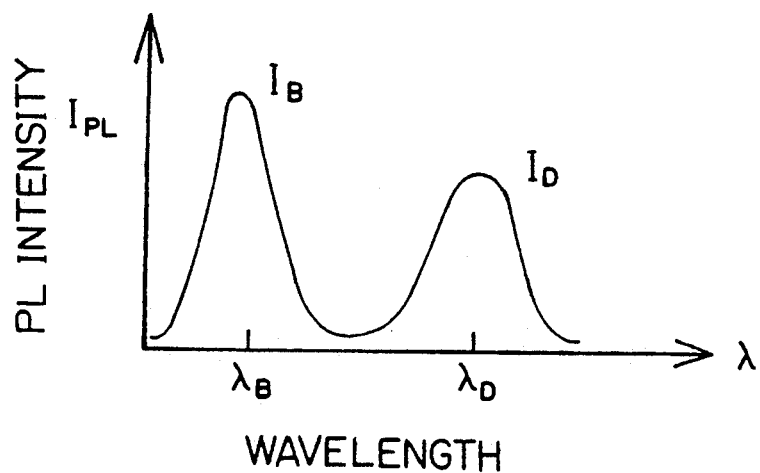
FIG. 2 is a graph showing a PL spectrum of a deep level PL intensity ($I_D$) at a wavelength of $\lambda_D$ and a band edge PL intensity ($I_B$) at a wavelength of $\lambda_B$ obtained in a semiconductor wafer by the use of the apparatus mentioned above in accordance with the room-temperature PL process.

In the apparatus of evaluation described above, the PL spectrum describing the deep level PL intensity ($I_D$) at the wavelength of $\lambda_D$ and the band edge PL intensity ($I_B$) at the wavelength of $\lambda_B$ as illustrated in FIG. 2 is obtained on the basis of the wavelength of the spectroscope 15 and the intensity of the PL signal from the amplifier 18 as described previously.

When the spectroscope 15 mentioned above is fixed at the wavelength $\lambda_D$ and, at the same time, the X-Y stage 11 and consequently the semiconductor wafer 12 as a sample are driven as controlled with the deep level PL intensity ($I_D$) as a function of the coordinates (X, Y) of the X-Y stage 11, therefore, the surface of the wafer 12 is automatically scanned by the excited laser beam 14 from the laser beam source 13 and the wafer map ($M_D$) of the deep level PL intensity ($I_D$) is produced. The mapping data ($M_D$) thus obtained are set to memory in the computer 19.

When the spectroscope 15 is fixed at the wavelength $\lambda_B$ and the procedure described above is repeated, the wafer map ($M_B$) of the band edge PL intensity ($I_B$) is produced. The mapping data ($M_B$) thus obtained are similarly set to memory in the computer 19.

Subsequently, in the computer 19, the operation between the set data ($M_D$) and the set data ($M_B$) is executed as indicated by the following [formula 6]to obtain the wafer map ($M_N$) of the relative value of deep level concentration. The mapping data ($M_N$) thus obtained are also set to memory in the computer 19.

$$M_D/M_B{}^\nu \quad \text{[Formula 6]}$$

As respects the numerical value of in the [formula 6], it suffices to adopt ($\nu = 1$) where the carrier excitation is adjusted only to a feeble extent such that the band edge PL intensity ($I_B$) is proportional to the 1.5th power of the power (P) of the excited laser beam 14 from the laser beam source 13 [$I_B \alpha P^{1.5}$] or to adopt ($\nu = 0.5$) where the excitation is adjusted to a high extent such that the intensity ($I_B$) is proportional to the second power of the laser power (P) [$I_B \alpha P^2$]. The numerical value may be empirically set between 0.5 and 1 where the excitation is made halfway between the feeble extent and the high extent mentioned above.

The set data ($M_N$) obtained as described above, therefore, indicate the distribution of the relative deep level concentration pertaining to the PL of the intensity ($I_D$) mentioned above.

Now, the method of evaluation contemplated by this invention will be described more specifically with reference to specific working examples of the invention to be cited below.

EXAMPLE 1

Figure 3:
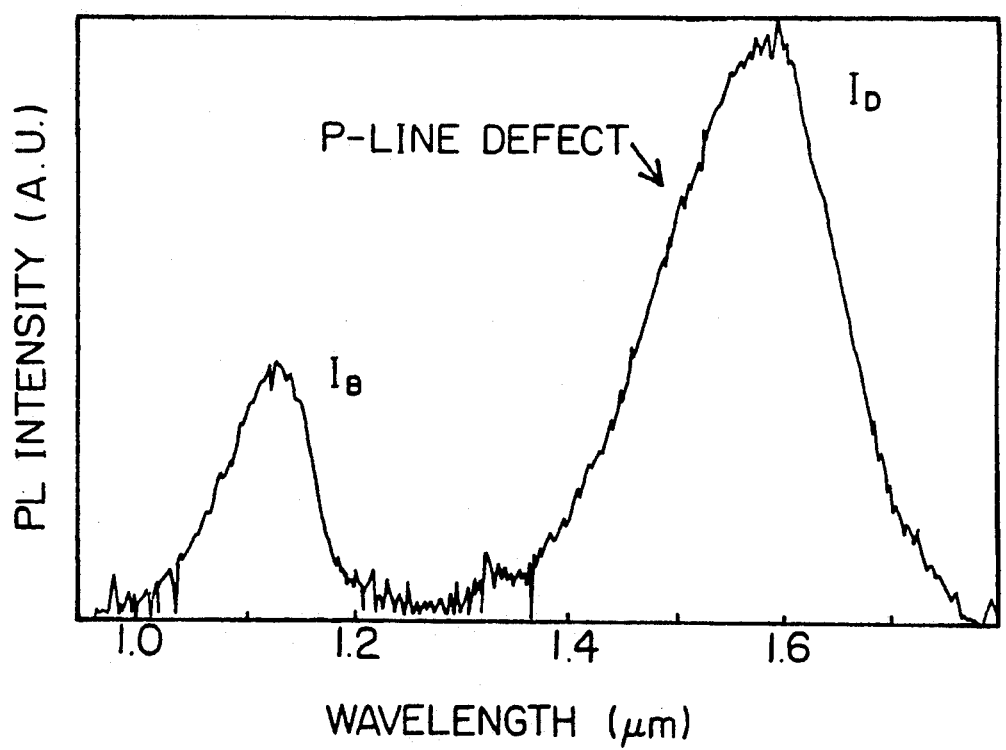
FIG. 3 is a graph showing a PL spectrum obtained by the room-temperature PL process of a wafer of the Czochralski (CZ)-grown Si single crystal prepared by 24 hours' heating at 450° C. in Example 1 of this invention.

FIG. 3 is a PL spectrum obtained by the room-temperature PL process of a semiconductor wafer prepared by subjecting a CZ-grown Si single crystal to a 24 hours' heat treatment at 450° C.

In the PL spectrum of FIG. 3, the peak in the neighborhood of a wavelength of 1.1 μm represents the band edge luminescence and the PL intensity thereof is ($I_B$) and the peak in the neighborhood of a wavelength of 1.6 μm represents the PL of deep level (equivalent to P-line) and the PL intensity thereof is ($I_D$).

The semiconductor wafer subjected to this measurement has a diameter of 10 cm and the diameter of the laser beam is 1 mm.

Figure 4A:
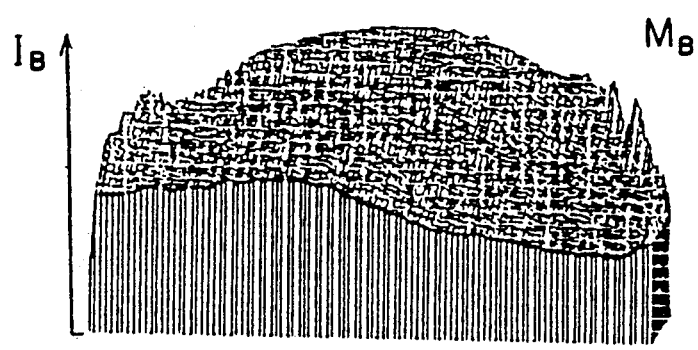
FIG. 4a is a partially sectioned perspective view of a three-dimensional map ($M_B$) obtained by measuring a band edge PL intensity ($I_B$) of the semiconductor wafer of Example 1 by the room-temperature PL process and mapping the results of the measurement.
Figure 4B:
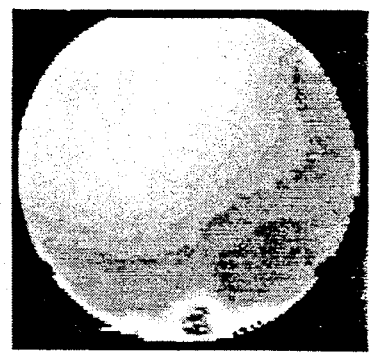
Figure 4D:
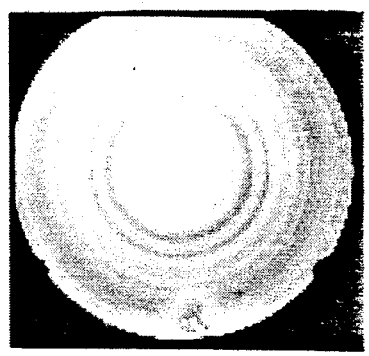
FIG. 4d is a plane view illustrating in monochromic concentration the intensity distribution of $I_D$ in the map ($M_D$) of FIG. 4c.

The wafer map ($M_B$) of the band edge PL intensity ($I_B$) mentioned above is as shown in FIG. 4a and FIG. 4b. By the same token, the wafer map ($M_D$) of the deep level PL intensity ($I_D$) mentioned above is as shown in FIG. 4c and FIG. 4d.

In the present measurement, the band edge PL intensity ($I_B$) is proportional to the second power of the laser power (P), indicating that the excitation is adjusted to a high extent. The wafer map ($M_B$) indicates the distribution due to a spatial ununiformity of the carrier lifetime ($\tau$). This lifetime distribution has an effect thereof to bear on the distribution ($M_D$) of the deep level PL intensity ($I_D \alpha N_D \tau$).

Figure 4F:
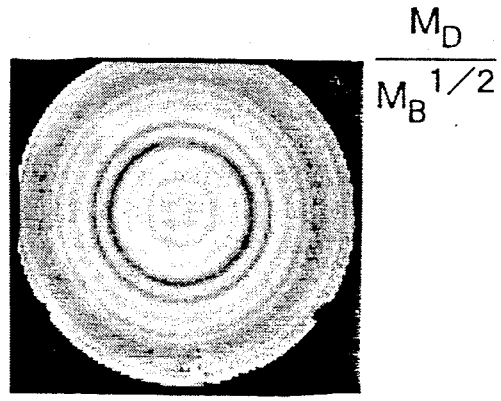
FIG. 4f is a plane view illustrating in monochromic concentration a distribution of the numerical value of $I_D/I_B^{\frac{1}{2}}$ of the map ($M_N$) of FIG. 4e.
Figure 4C:
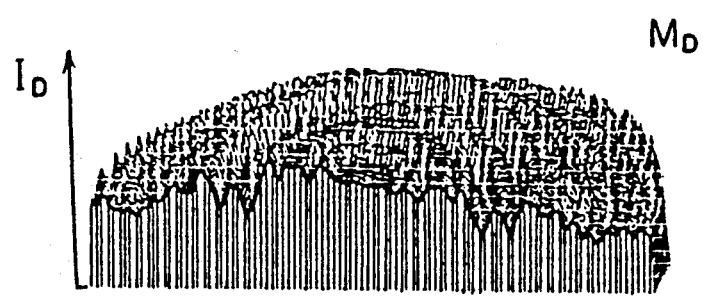
FIG. 4c is a partially sectioned perspective view of a three-dimensional map ($M_D$) obtained by measuring the deep level PL intensity ($I_D$) of the semiconductor wafer of Example 1 by the room-temperature PL process and mapping the results of the measurement.
Figure 4E:
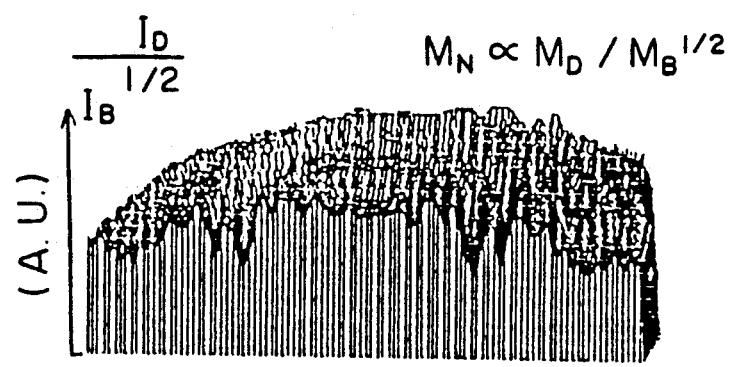
FIG. 4e is a partially sectioned perspective view of a three-dimensional map ($M_N \alpha M_D/M_B^{\frac{1}{2}}$) obtained by calculating the numerical values of $I_D/I_B^{\frac{1}{2}}$ at given points of measurement from the $I_B$'s of FIG. 4a and FIG. 4b and the $I_D$'s of FIG. 4c and FIG. 4d mentioned above and mapping the results of the calculation.

The distribution ($M_N \alpha M_D/M_B{}^{\frac{1}{2}}$) which results from the division of the deep level PL intensity ($I_D \alpha N_D \tau$) by the ½th power of the band edge PL intensity ($I_B \alpha \tau^2$) determines the distribution of the relative numerical value of the P-line defect concentration ($N_D$) and is relieved of the ununiform spatial effect of the carrier life time ($\tau$) as shown in FIG. 4e and FIG. 4f.

EXAMPLE 2

Figure 5:
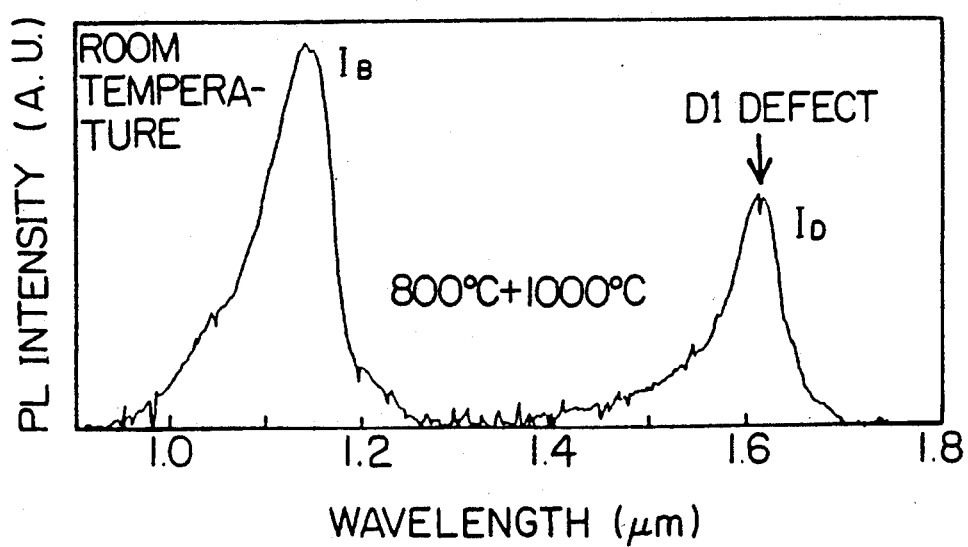
FIG. 5 is a graph showing a room-temperature PL spectrum obtained of a wafer prepared by subjecting a CZ-grown Si single crystal to oxygen precipitation by a two-stage heat treatment in Example 2 of this invention.

FIG. 5 represents a PL spectrum obtained by the room-temperature PL process of a sample wafer prepared by subjecting a CZ-grown Si single crystal to oxygen precipitation by a two-stage heat treatment (in the atmosphere of nitrogen at 800° C. for four hours and in the atmosphere of $O_2$ at 1000° C. for 16 hours).

In the PL spectrum of FIG. 5, the band edge luminescence having a peak in the neighborhood of a wavelength of 1.1 μm and the luminescence (D1-line) of deep level defect due to the oxygen precipitation having a peak in the neighborhood of a wavelength of 1.6 μm is observed.

Figure 6:
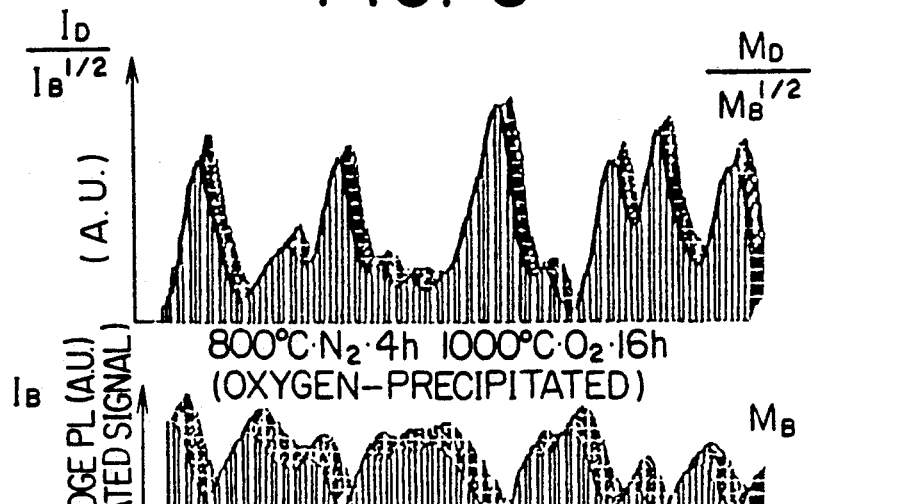
FIG. 6(a) and FIG. 6(b) are graphs illustrating microscopic distributions of [Oi] in the direction of axis of growth before and after the heat treatment of Example 2.
FIG. 6(c) is a graph showing a distribution of deep level PL intensity ($I_D$) in the direction of axis of growth.
FIG. 6(d) is a graph showing a distribution of a band edge PL intensity ($I_B$) in the direction of axis of growth.
FIG. 6(e) is a graph showing a distribution of numerical values of $I_D/I_B^{\frac{1}{2}}$ calculated from the $I_D$ and $I_B$ in the direction of axis of growth.
FIG. 6(f) is an X-ray topograph after oxygen precipitation.
Figure 6:
Figure 6:
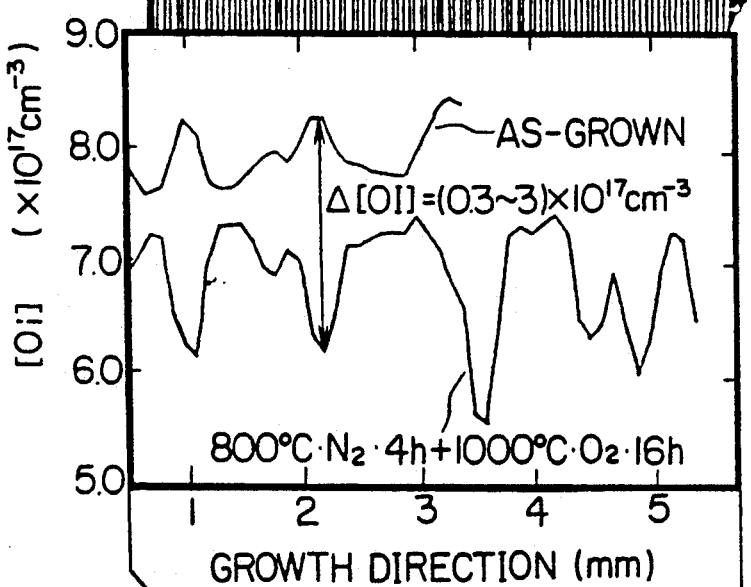
Figure 6:
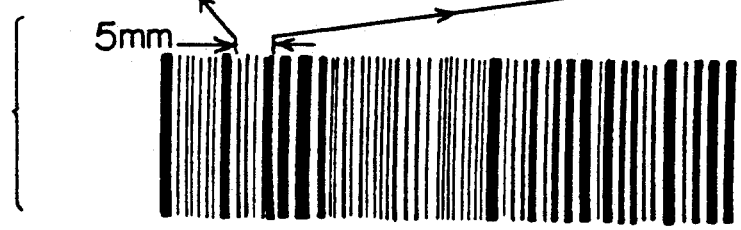

The PL intensity distribution is obtained by scanning the sample with a laser beam having a diameter of 100 μm and using a fixed step of 100 μm. The measuring time spent at a point is in the range between 0.03 and 0.5 second. A review of fine distribution in the 5 mm distance in the direction of axis of growth as shown in the X-ray topograph of FIG. 6(f) reveals that the results of actual measurement of the maps in the wafer of the band edge PL intensity ($I_B$) and the deep level PL intensity ($I_D$) are as shown respectively in FIG. 6(d) and (c). Again in this case, the band edge PL intensity ($I_B$) is roughly proportional to the second power of the laser power (P), indicating that the excitation is adjusted to a high extent. The distribution of relative deep level concentration in this case, therefore, is expressed as ($M_D/M_B^{\frac{1}{2}}$). FIG. 6(e) illustrates the distribution of the numerical value of ($M_D/M_B^{\frac{1}{2}}$) calculated by the computer. This distribution shows a very close agreement with the distribution of the amount of precipitated oxygen, Δ[Oi] [the difference between the curves (a) and (b)].

This close agreement strongly supports the conclusion that the distribution of the numerical value of ($M_D/M_B^{\frac{1}{2}}$) shown in FIG. 6(e) constitutes itself the distribution of relative deep level defect concentration due to the precipitation of oxygen.

EXAMPLE 3

Figure 7A:
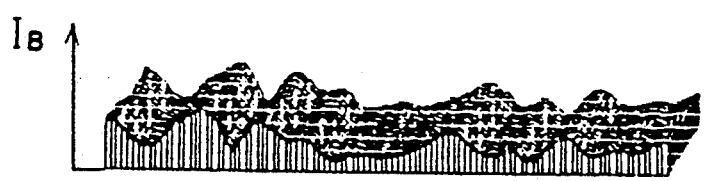
FIG. 7a, FIG. 7b, and FIG. 7c are graphs showing distributions of relevant intensities ($I_B$) and ($I_D$) and a distribution of ($I_D/I_B^{\frac{1}{2}}$) *obtained in the wafer with a thermal oxide surface layer immediately after the heat treatment.*
Figure 7B:
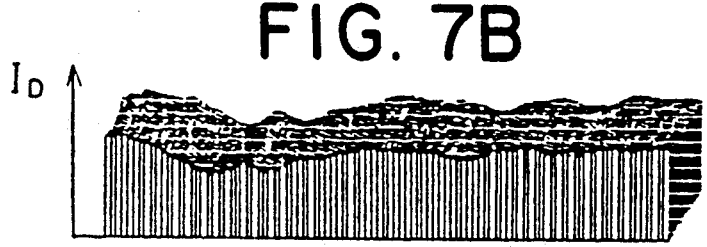
Figure 7C:
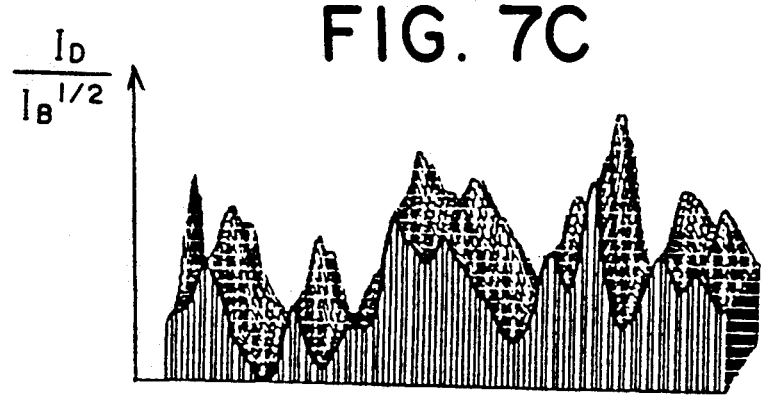
Figure 8A:
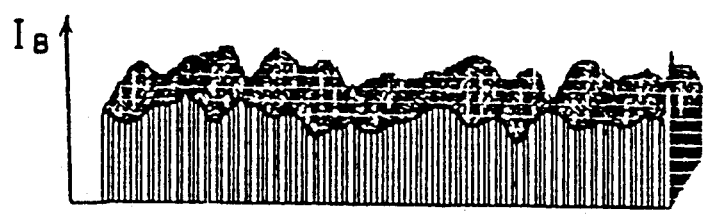
FIG. 8a, FIG. 8b, and FIG. 8c are graphs showing distributions of relevant intensities ($I_B$) and ($I_D$) and a distribution of ($I_D/I_B^{\frac{1}{2}}$) obtained in the wafer after removal of the thermal oxide layer.
Figure 8B:
Figure 8C:
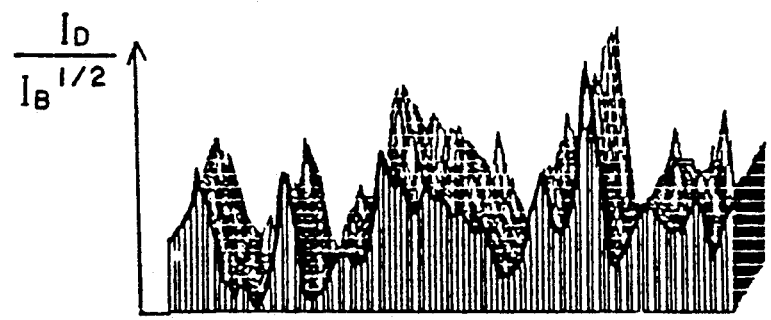

FIG. 7 (a-b) and FIG. 8 (a-c) illustrate the results of evaluation of the distribution of intensity of PL spectrum obtained of the oxygen-precipitated CZ-grown Si single crystal in absolutely the same manner as in Example 2 by the room-temperature PL process in the same 5 mm distance in the direction of axis of growth. Specifically, FIG. 7a, FIG. 7b, and FIG. 7c represent the results of measurement of the intensities ($I_B$), ($I_D$), and ($I_D I_B^{\frac{1}{2}}$) respectively in the wafer with a thermal oxide surface layer immediately after the heat treatment and FIG. 8a, FIG. 8b, and FIG. 8c the results of measurement of the intensities ($I_B$), ($I_D$), and ($I_D/I_B^{\frac{1}{2}}$) respectively after removal of the thermal oxide layer.

Comparison of the intensities of FIG. 7b and FIG. 8b clearly reveals that the distribution of the intensity ($I_D$) of the luminescence (D1-line) of deep level defect is conspicuously varied by the state of surface of the sample wafer and that it generally fails to represent the distribution of deep level concentration.

Here again, the band edge PL intensity ($I_B$) is roughly proportional to the second power of the laser power (P) and, therefore, the distribution of ($I_D/I_B^{\frac{1}{2}}$) ought to constitute itself the distribution of relative concentration of (D1-line) defect. In fact, the distribution of ($I_D I_B^{\frac{1}{2}}$) of FIG. 7c and that of FIG. 8c are substantially equal in spite of the difference in the surface state of sample wafer and the difference in the distribution of intensity ($I_D$).

This substantial equality may well be regarded as a natural consequence of the fact that the distribution of ($I_D/I_B^{\frac{1}{2}}$) represents the deep level (D1-line) concentration of a bulk crystal.

It is clear from the description given thus far that by the method of this invention, the spatial distribution of relative deep level concentration near the surface of a semiconductor wafer can be obtained in a semiconductor in which the carrier lifetime is varied spatially in the wafer thereof. The laser beam to be used for the measurement is allowed to have an extremely small diameter like 100 μm. In the process of scanning with this laser beam, the step width may be as small as 100 μm, for example. Further, since $I_D$ and $I_B$ are the values to be obtained by the measurement made at one and the same point, the relative concentration obtained in the wafer enjoys extremely high accuracy with respect to that position. Since the time required for the measurement of $I_D$ and $I_B$ is as brief as 0.01 to 1 second per point of measurement, the spatial distribution of the relative deep level concentration in the semiconductor crystal of a semiconductor wafer can be obtained in an extremely short time with high sensitivity.

While there have been shown and described present preferred embodiments of the invention, it is to be distinctly understood that the invention is not limited thereto but may be otherwise variously embodied and practiced within the scope of the following claims.

What is claimed is:

1. A method for the evaluation of distribution of deep level concentration near the surface of a semiconductor wafer under test, comprising the steps of:

scanning the surface of said semiconductor wafer in the X and Y direction with a laser beam for carrier excitation from a laser beam source in accordance with the room-temperature photoluminescence (PL) process;

measuring wafer map ($M_D$) of photoluminescence intensity (deep level PL intensity) ($I_D$) due to deep level;

measuring wafer map ($M_B$) of band edge PL intensity ($I_B$) in said semiconductor wafer; and dividing said wafer map ($M_D$) of the said PL intensity ($I_D$) by the $v$'th power of said wafer map ($M_B$) of PL intensity ($I_B$) {the magnitude of the $v$'th power representing the numerical value obtained by empirically confirming the dependence of the band edge PL intensity ($I_B$) on the power of the excitation laser beam} thereby determining the spatial distribution ($M_N$) of the relative value of deep level concentration ($N_D$).

* * * * *